(12) United States Patent
Gill et al.

(10) Patent No.: US 11,559,696 B2
(45) Date of Patent: Jan. 24, 2023

(54) IMPLANTABLE MEDICAL DEVICE FOR ARRHYTHMIA DETECTION

(71) Applicant: Pacesetter, Inc., Sylmar, CA (US)

(72) Inventors: Jong Gill, Valencia, CA (US); Gene Bornzin, Santa Monica, CA (US)

(73) Assignee: Pacesetter, Inc., Sylmar, CA (US)

( * ) Notice: Subject to any disclaimer, the term of this patent is extended or adjusted under 35 U.S.C. 154(b) by 12 days.

(21) Appl. No.: 17/396,804

(22) Filed: Aug. 9, 2021

(65) Prior Publication Data

US 2021/0361959 A1 Nov. 25, 2021

Related U.S. Application Data

(63) Continuation of application No. 16/425,790, filed on May 29, 2019, now Pat. No. 11,116,989.

(51) Int. Cl.
| | |
|---|---|
| *A61N 1/05* | (2006.01) |
| *A61N 1/36* | (2006.01) |
| *A61N 1/375* | (2006.01) |
| *A61N 1/39* | (2006.01) |
| *A61B 5/361* | (2021.01) |
| *A61N 1/365* | (2006.01) |
| *A61N 1/362* | (2006.01) |
| *A61B 5/352* | (2021.01) |

(Continued)

(52) U.S. Cl.
CPC ............ *A61N 1/3962* (2013.01); *A61B 5/361* (2021.01); *A61N 1/3756* (2013.01); *A61B 5/352* (2021.01); *A61B 5/364* (2021.01); *A61B 5/366* (2021.01); *A61N 1/056* (2013.01); *A61N 1/3622* (2013.01); *A61N 1/36542* (2013.01)

(58) Field of Classification Search
CPC .... A61N 1/3962; A61N 1/3756; A61N 1/056; A61N 1/3622; A61N 1/36542; A61B 5/361; A61B 5/352; A61B 5/364; A61B 5/366; A61B 8/0883; A61B 2560/0238; A61B 5/1102; A61B 2562/0204; A61B 2562/0219; A61B 5/686; A61B 2505/07; A61B 5/7221
See application file for complete search history.

(56) References Cited

U.S. PATENT DOCUMENTS 6,466,821 B1  10/2002  Pianca et al.
7,559,900 B2   7/2009  Gillberg
(Continued)

*Primary Examiner* — Carl H Layno
*Assistant Examiner* — Anh-Khoa N Dinh
(74) *Attorney, Agent, or Firm* — The Small Patent Law Group LLC; Dean D. Small

(57) ABSTRACT

A computer implemented method for determining heart arrhythmias based on cardiac activity that includes under control of one or more processors of an implantable medical device (IMD) configured with specific executable instructions to obtain far field cardiac activity (CA) signals at electrodes located remote from the heart, and obtain acceleration signatures, at an accelerometer of the IMD, indicative of heart sounds generated during the cardiac beats. The IMD is also configured with specific executable instructions to declare a candidate arrhythmia based on a characteristic of at least one R-R interval from the cardiac beats, and evaluate the acceleration signatures for ventricular events (VEs) to re-assess a presence or absence of at least one R-wave from the cardiac beats and based thereon confirming or denying the candidate arrhythmia.

20 Claims, 8 Drawing Sheets

(51) Int. Cl.
*A61B 5/364* (2021.01)
*A61B 5/366* (2021.01)

(56) References Cited

U.S. PATENT DOCUMENTS

| | | |
|---|---|---|
| 7,682,316 B2 | 3/2010 | Anderson et al. |
| 9,616,239 B2 | 4/2017 | Maskara et al. |
| 2008/0243200 A1* | 10/2008 | Scinicariello ........ A61N 1/3704 607/4 |
| 2011/0201969 A1 | 8/2011 | Hatlestad et al. |
| 2016/0067486 A1 | 3/2016 | Brown et al. |
| 2017/0209061 A1 | 7/2017 | Thakur et al. |
| 2017/0273589 A1 | 9/2017 | Sarkar et al. |
| 2018/0078779 A1 | 3/2018 | An et al. |

* cited by examiner

IMPLANTABLE MEDICAL DEVICE FOR ARRHYTHMIA DETECTION

REFERENCE TO RELATED APPLICATIONS

The present application is a continuation application of, and claims priority to, U.S. application Ser. No. 16/425,790, Titled "IMPLANTABLE MEDICAL DEVICE FOR ARRHYTHMIA DETECTION" which was filed on 29 May 2019 (now U.S. Pat. No. 11,116,989), the complete subject matter of which is expressly incorporated herein by reference in its entirety.

BACKGROUND

Embodiments herein generally relate to an implantable medical device (IMD), and more particularly to an IMD that utilizes heart sounds in connection with arrhythmia detection.

Various types of implantable medical devices (IMDs) are utilized today, including IMDs that deliver therapy and IMDs that merely monitor a patient. IMDs that do not delivery therapy are also referred to as an implantable cardiac monitor (ICM). An ICM is a small medical device placed beneath your chest muscle to continuously monitor cardiac activity and record electrocardiograms (ECGs) automatically. An ICM includes one or more combinations of electrodes to sense and record the cardiac activity. As the ICM records cardiac activity continuously and/or periodically, the patient will move between various states and postures.

ICMs are often utilized to help clinicians diagnose and treat abnormal heart activities that may be the cause of symptoms such as palpitations (e.g., noticeably rapid, strong, or irregular heartbeats due to agitation, exertion, or illness), lightheadedness, dizziness, or more importantly syncope (fainting). The abnormal heart activities include bradycardia arrhythmia (e.g., slow heart rate), tachycardia (e.g., fast heart rate), asystole (e.g., no electrical heart activity), atrial or ventricular arrhythmias (e.g., problems with rate or rhythm of heartbeat), or the like.

However, ICMs may incorrectly interpret the cardiac activity signals and declare a false arrhythmia. A desire remains to improve the reliability of arrhythmia detection and to reduce the number of false positive arrhythmia declarations. The reliability of the arrhythmia diagnosis is dependent in part on the nature and quality of the cardiac activity signals recorded. The nature and quality of the recorded cardiac activity signals is dependent on various factors, including a position and orientation of the ICM and/or IMD. The ICM includes electrodes physically mounted within the housing of the ICM, and therefore when the ICM housing shifts in position and/or orientation, the electrodes similarly shift. Some IMDs that deliver therapy also include electrodes physically mounted within the housing (e.g., leadless IMDs), and when the IMD housing shifts in position and/or orientation, the electrodes similarly shift.

A three-dimensional (3-D) accelerometer may detect rotation based on the position and/or orientation of the ICM and more generally the IMD. For example, the 3-D accelerometer may detect a difference in the position and/or orientation of the IMD, based on the heart sound difference, which may be used in conjunction to determine a change in position of the IMD. Due to the linear shape and small size of an IMD, the device may rotate or otherwise move within a subcutaneous implant region. IMD rotation, translation, and motion may cause the device to inappropriately detect heart signals by altering the R-wave amplitudes and morphologies. Also, changes in the position and orientation of the IMD, and sensing electrodes, may alter the morphology of the recorded cardiac activity signals, including, among other things, the amplitude of the P waves, R waves, T waves and the like. Similarly, the effects of position changes to the heart sound signal quality may be affected if the device pocket for the implantable cardiac monitoring (ICM) device is loose, or the device pocket is relatively soft in obese patients.

Similarly, the 3-D accelerometer can also provide varying results based on the patient position. For example, patients change position while monitoring occurs during sleep, i.e., sleeping on left, sleeping on right, supine, prone, 45 degree inclined, etc., which can shift the device away from the previously held optimal position, leading to a potential degradation in heart sound signal quality.

BRIEF SUMMARY

In accordance with embodiments herein, a computer implemented method for determining heart arrhythmias based on cardiac activity that includes under control of one or more processors of an implantable medical device (IMD) configured with specific executable instructions to obtain far field cardiac activity (CA) signals at electrodes located remote from the heart, and obtain acceleration signatures, at an accelerometer of the IMD, indicative of heart sounds generated during the cardiac beats. The IMD is also configured with specific executable instructions to declare a candidate arrhythmia based on a characteristic of at least one R-R interval from the cardiac beats, and evaluate the acceleration signatures for ventricular events (VEs) to re-assess a presence or absence of at least one R-wave from the cardiac beats and based thereon confirming or denying the candidate arrhythmia.

Optionally, evaluating the acceleration signatures includes determining at least one VE feature of interest of the acceleration signatures and comparing the at least one VE feature of interest with predetermined VE confirmation criteria related to the at least one VE feature of interest. Alternatively, the at least one VE feature of interest includes amplitude variability of the acceleration signatures, or variability of a QRS to heart sound interval.

Optionally, the candidate arrhythmia is denied when the analysis of the acceleration signatures identifies a first heart sound indicating a presence of a corresponding VE during an interval between successive first and second R waves in the at least one R-R interval.

In another aspect, the method further comprises evaluating the acceleration signatures to identify heart sound (HS) indicated VEs to determine whether the declaring of the candidate arrythmia is responsive to at least one of under-sensing or over-sensing R-waves in the far field CA signals. Optionally, the HS includes at least one VE feature of interest that includes at least one of i) turbulence due to closure of a mitral valve and/or tricuspid value at a start of systole, ii) closure of aortic valve and/or pulmonic valve at an end of systole, iii) contraction (S1), iv) relaxation (S2), v) blood flowing into a ventricle (S3), or vi) hypertension (S4). Alternatively, the VE feature of interest of the HS includes at least one of an S1 amplitude, an S1 frequency, a peak to peak timing between heart sounds in the acceleration signatures, or a ratio of heart sounds.

Optionally, the obtaining the acceleration signatures further includes in connection with a calibration procedure, obtaining calibration acceleration signatures, at the accelerometer of the IMD, indicative of heart sounds generated in connection with first and second postures of a patient; and after the calibration procedure, utilizing the calibration acceleration signatures to determine an axis of the accelerometer associated with a current posture, and obtaining confirmation acceleration signatures along the axis of the accelerometer in connection with the analyzing the far field CA signals. Alternatively, the method also includes determining a filter for the axis of the accelerometer determined based on the calibration acceleration signatures; and filtering the confirmation acceleration signatures based on the filter. Optionally, determining a filter for the axis of the accelerometer includes determining a signal to noise ratio for the axis of the accelerometer for a feature of interest of a heart sound.

In another aspect, the far field CA signals indicative of first and second cardiac beats occurring while the IMD is in different first and second IMD orientations relative to gravitational force, and the obtaining the acceleration signatures comprises obtaining first and second acceleration signatures along first and second axes of the accelerometer associated with the corresponding first and second IMD orientations.

In accordance with other embodiments herein a system is provided for determining heart arrhythmias based on cardiac activity. The system includes one or more processors, and a memory coupled to the one or more processors, wherein the memory stores program instructions. The program instructions are executable by the one or more processors to obtain far field cardiac activity (CA) signals at electrodes located remote from the heart, obtain acceleration signatures, at an accelerometer of the IMD, indicative of heart sounds generated during the cardiac beats, declare a candidate arrhythmia based on a characteristic of at least one R-R interval from the cardiac beats, and evaluate the acceleration signatures for ventricular events (VEs) to re-assess a presence or absence of at least one R-wave from the cardiac beats and based thereon confirming or denying the candidate arrhythmia.

Optionally, the evaluation operation includes identifying at least one an amplitude variability of the acceleration signatures, or a variability of a QRS to S1 heart sound interval. Alternatively, the evaluation operation further comprises identifying a variability relation between the amplitude variability and the variability of the QRS to S1 heart sound interval and comparing the variability relation to a threshold line that separates atrial fibrillation (AF) arrhythmias and normal sinus rhythms.

Optionally, the one or more processors are configured to evaluate the acceleration signatures to identify heart sound (HS) indicated VEs to determine whether the declaring of the candidate arrythmia is responsive to at least one undersensing or over-sensing of R-waves in the far field CA signals. In another aspect, to obtain the acceleration signatures, the program instructions are executable by the one or more processors to in connection with a calibration procedure, obtain calibration acceleration signatures, at the accelerometer of the IMD, indicative of a heart sound generated in connection with first and second postures of a patient. Additionally, after the calibration procedure, utilize the calibration acceleration signatures to determine an axis of the accelerometer associated with a current posture, and obtain confirmation acceleration signatures along the axis of the accelerometer in connection with the analyzing the far field CA signals.

Optionally, the program instructions are executable by the one or more processors to evaluate the acceleration signatures to determine a filter for the axis of the accelerometer based on the calibration acceleration signatures, and filter the confirmation acceleration signatures based on the filter.

In another aspect, to determine a filter for the axis of the accelerometer the program instructions are executable by the one or more processors to determine a signal to noise ratio for the axis of the accelerometer for a feature of interest of the heart sound. Optionally, to filter the confirmation acceleration signatures based on the filter the program instructions are executable by the one or more processors to switch a setting of a bandpass filter. In another aspect, the feature of interest of the HS includes at least one VE feature of interest that includes at least one of i) turbulence due to closure of a mitral valve and/or tricuspid value at a start of systole, ii) closure of aortic valve and/or pulmonic valve at an end of systole, iii) contraction (S1), iv) relaxation (S2), v) blood flowing into a ventricle (S3), or vi) hypertension (S4).

In accordance with yet other embodiments herein a computer implemented method is provided for determining heart arrhythmias, that includes under control of one or more processors of an implantable medical device (IMD) configured with specific executable instructions. The method includes obtaining acceleration signatures, at an accelerometer of the IMD, indicative of heart sounds generated during cardiac beats, evaluating the acceleration signatures by determining at least one feature of interest of the acceleration signatures, wherein the at least one feature of interest includes amplitude variability of the acceleration signatures, or variability of a QRS to S1 heart sound interval, comparing the at least one feature of interest with predetermined arrythmia criteria, and declaring an arrhythmia based on the at least one feature of interest.

Optionally, the determining comprises determining both the amplitude variability and the variability of the QRS to S1 heart sound interval, and wherein the comparing comprises identifying a variability relation between the amplitude variability and the variability of the QRS to S1 heart sound interval and comparing the variability relation to a threshold line that separates atrial fibrillation (AF) arrhythmias and normal sinus rhythms.

In another aspect the VE feature of interest includes at least one of an S1 amplitude, an S1 frequency, a peak to peak timing between heart sounds in the acceleration signatures, or a ratio of heart sounds. Optionally, the obtaining the acceleration signatures also includes in connection with a calibration procedure, obtaining calibration acceleration signatures, at the accelerometer of the IMD, indicative of heart sounds generated in connection with first and second postures of a patient, and after the calibration procedure utilizing the calibration acceleration signatures to determine an axis of the accelerometer associated with a current posture, and obtaining confirmation acceleration signatures along the axis of the accelerometer. In another aspect the method also includes determining an axis of the accelerometer associated with a current IMD orientation, wherein the obtaining the acceleration signatures comprises obtaining the acceleration signatures along the axes determined.

DETAILED DESCRIPTION

Figure 1:
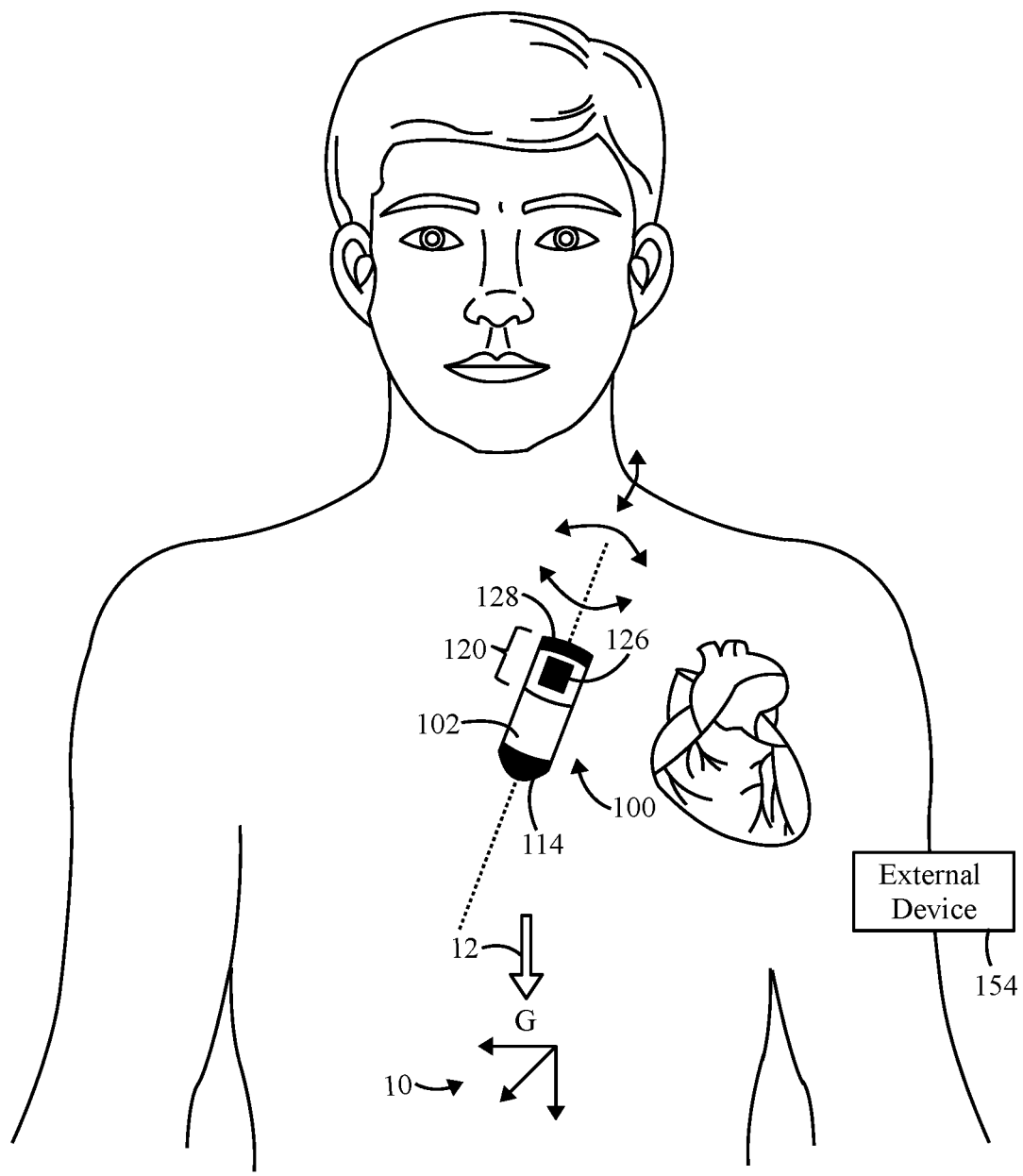
FIG. 1 illustrates an implantable cardiac monitoring device (ICM) intended for subcutaneous implantation at a site near the heart in accordance with embodiments herein.

The terms "state" and "patient state" refer to types of activity currently experienced by a patient, including a stationary state, rest state, exercise state, walking state, and the like.

The terms "posture" and "patient posture" refer to posture positions of a patient, including a standing posture, sitting posture, supine posture, prone posture, horizontal side posture (e.g., laying on one's side), 45 degree incline, and the like.

The term "IMD location" refers to a position of an IMD, with respect to a reference position, and an orientation of the IMD with respect to a reference orientation. The IMD location may be determined relative to gravitational force. The reference position and orientation may be relative to a global coordinate system. By way of example, an IMD may translationally drift along one or more linear axis (e.g., X, Y and Z directions) from the reference position. Additionally or alternatively, the IMD may rotationally drift along one or more rotational axis (e.g., pitch, yaw and roll directions) from the reference orientation.

The terms "cardiac activity signal", "cardiac activity signals", "CA signal" and "CA signals" (collectively "CA signals") are used interchangeably throughout to refer to an analog or digital electrical signal recorded by two or more electrodes positioned subcutaneous or cutaneous, where the electrical signals are indicative of cardiac electrical activity. The cardiac activity may be normal/healthy or abnormal/arrhythmic. Non-limiting examples of CA signals include ECG signals collected by cutaneous electrodes, and EGM signals collected by subcutaneous electrodes.

The phrase "in connection with treating a heart condition" and similar phrases, as used herein include, but are not limited to, delivering an electrical stimulation or drug therapy to a heart condition. By way of example, treating a heart condition may include, in whole or in part, i) identifying a progression of heart failure over time; ii) confirming an arrhythmia identified by an arrhythmia detection process; iii) instructing the patient to perform a posture recalibration procedure and/or iv) delivering a therapy.

The terms "beat" and "cardiac event" are used interchangeably and refer to both normal and/or abnormal events.

The terms "normal" and "sinus" are used to refer to events, features, and characteristics of, or appropriate to, a heart's healthy or normal functioning.

The terms "abnormal," or "arrhythmic" are used to refer to events, features, and characteristics of, or appropriate to, an unhealthy or abnormal functioning of the heart.

The term "real-time" refers to a time frame contemporaneous with normal or abnormal episode occurrences. For example, a real-time process or operation would occur during or immediately after (e.g., within minutes or seconds after) a cardiac event, a series of cardiac events, an arrhythmia episode, and the like.

The term "obtains" and "obtaining", as used in connection with data, signals, information and the like, include at least one of i) accessing memory of an external device or remote server where the data, signals, information, etc. are stored, ii) receiving the data, signals, information, etc. over a wireless communications link between the ICM and a local external device, and/or iii) receiving the data, signals, information, etc. at a remote server over a network connection. The obtaining operation, when from the perspective of an ICM, may include sensing new signals in real time, and/or accessing memory to read stored data, signals, information, etc. from memory within the ICM. The obtaining operation, when from the perspective of a local external device, includes receiving the data, signals, information, etc. at a transceiver of the local external device where the data, signals, information, etc. are transmitted from an IMD and/or a remote server. The obtaining operation may be from the perspective of a remote server, such as when receiving the data, signals, information, etc. at a network interface from a local external device and/or directly from an IMD. The remote server may also obtain the data, signals, information, etc. from local memory and/or from other memory, such as within a cloud storage environment and/or from the memory of a workstation or clinician external programmer.

The terms "device shift" and "IMD shift," as used herein, refer to a change in position and/or orientation of an IMD within a subcutaneous implant region. By way of example, an IMD drift may occur when an IMD moves in one or more of six degrees of freedom within the subcutaneous implant region. As a further example, a reference point and/or longitudinal axis of an IMD may move in an X, Y and/or Z direction and/or rotate in a pitch, yaw and/or tilt direction with respect to a reference point in a patient (e.g., a reference point on the heart).

Embodiments may be implemented in connection with one or more implantable medical devices (IMDs), including IMDs that include an ICM functionality. Non-limiting examples of IMDs include one or more of neurostimulator devices, implantable leadless monitoring and/or therapy devices. For example, the IMD may represent a cardiac monitoring device, pacemaker, cardioverter, cardiac rhythm management device, defibrillator, neurostimulator, leadless monitoring device, leadless pacemaker and the like. For example, the IMD may include one or more structural and/or functional aspects of the device(s) described in U.S. Pat. No. 9,333,351 "Neurostimulation Method And System To Treat Apnea" and U.S. Pat. No. 9,044,610 "System And Methods For Providing A Distributed Virtual Stimulation Cathode For Use With An Implantable Neurostimulation System", which are hereby incorporated by reference. Additionally or alternatively, the IMD may include one or more structural and/or functional aspects of the device(s) described in U.S. Pat. No. 9,216,285 "Leadless Implantable Medical Device Having Removable And Fixed Components" and U.S. Pat. No. 8,831,747 "Leadless Neurostimulation Device And Method Including The Same", which are hereby incorporated by reference. Additionally or alternatively, the IMD may include one or more structural and/or functional aspects of the device(s) described in U.S. Pat. No. 8,391,980 "Method And System For Identifying A Potential Lead Failure In An Implantable Medical Device" and U.S. Pat. No. 9,232,485 "System And Method For Selectively Communicating With An Implantable Medical Device", which are hereby incorporated by reference.

FIG. 1 illustrates an implantable medical device (IMD) 100 intended for subcutaneous implantation at a site near the heart. The IMD 100 includes a pair of spaced-apart sense electrodes 114, 126 positioned with respect to a housing 102. The sense electrodes 114, 126 provide for detection of far field electrogram signals. Numerous configurations of electrode arrangements are possible. For example, the electrode 114 may be located on a distal end of the IMD 100, while the electrode 126 is located on a proximal side of the IMD 100. Additionally or alternatively, electrodes 126 may be located on opposite sides of the IMD 100, opposite ends or elsewhere. The distal electrode 114 may be formed as part of the housing 102, for example, by coating all but a portion of the housing with a nonconductive material such that the uncoated portion forms the electrode 114. In this case, the electrode 126 may be electrically isolated from the housing 102 electrode by placing it on a component separate from the housing 102, such as the header 120. Optionally, the header 120 may be formed as an integral portion of the housing 102. The header 120 includes an antenna 128 and the electrode 126. The antenna 128 is configured to wirelessly communicate with an external device 154 in accordance with one or more predetermined wireless protocols (e.g., Bluetooth, Bluetooth low energy, Wi-Fi, etc.).

The housing 102 includes various other components such as: sense electronics for receiving signals from the electrodes, a microprocessor for analyzing the far field CA signals, including assessing the presence of R-waves in cardiac beats occurring while the IMD is in different IMD locations relative to gravitational force, a loop memory for temporary storage of CA data, a device memory for long-term storage of CA data, sensors for detecting patient activity, including an accelerometer for detecting acceleration signatures indicative of heart sound, and a battery for powering components.

In at least some embodiments, the IMD 100 is configured to be placed subcutaneously utilizing a minimally invasive approach. Subcutaneous electrodes are provided on the housing 102 to simplify the implant procedure and eliminate a need for a transvenous lead system. The sensing electrodes may be located on opposite sides of the device and designed to provide robust episode detection through consistent contact at a sensor-tissue interface. The IMD 100 may be configured to be activated by the patient or automatically activated, in connection with recording subcutaneous ECG signals.

The IMD 100 senses far field, subcutaneous CA signals, processes the CA signals to detect arrhythmias and if an arrhythmia is detected, automatically records the CA signals in memory for subsequent transmission to an external device 154.

The IMD 100 is implanted in a position and orientation such that, when the patient stands, the IMD 100 is located at a reference position and orientation with respect to a global coordinate system 10 that is defined relative to a gravitational direction 12. For example, the gravitational direction 12 is along the Z-axis while the X-axis is between the left and right arms.

As explained herein, the IMD 100 includes electrodes that collect cardiac activity (CA) signals in connection with multiple cardiac beats and in connection with different IMD locations (e.g., different positions and/or different orientations). The IMD may change location within a subcutaneous pocket relative to an initial implant position through translation and/or rotation, such as i) moving up and down (elevating/heaving) within the subcutaneous pocket; ii) moving left and right (strafing/swaying); iii) moving forward and backward (walking/surging); iv) swiveling left and right (yawing); v) tilting forward and backward (pitching); and pivoting side to side (rolling). The IMD 100 also includes one or more sensors to collect device location information indicative of movement of the IMD 100 along one or more degrees of freedom, namely translational motion along X, Y, and Z directions, and/or rotationally motion along pitch, yaw and/or roll directions.

The IMD 100 also includes one or more sensors to collect acceleration signatures that are indicative of heart sounds produced at different points in a cardiac cycle. As described further herein, one or more processors of the IMD evaluate the acceleration signatures for ventricular events (VEs) to re-access the absence of an R-wave that exist when assessing the presence of R-waves in cardiac beats. Evaluation of the acceleration signatures includes determining one or more VE features of interest of the acceleration signatures and comparing each VE feature of interest with predetermined VE confirmation criteria related to the at least one VE feature of interest. In an example, the VE features of interest may include amplitude variability of the acceleration signatures, variability of a QRS to heart sound interval, a sensed R-wave, or the like. In another example, the acceleration signatures are evaluated to identify heart sound indicated VEs, and the heart sound indicated VEs are compared to results of the analysis of the far field CA signals to determine whether the analysis of the far field CA signals is performing at least one of under sensing or over sensing of R-waves in the far field CA signals. In an example, heart sounds include VE features of interest, including turbulence due to closure of a mitral valve and/or tricuspid value at a start of systole, closure of aortic valve and/or pulmonic valve at an end of systole, contraction (S1), relaxation (S2), blood flowing into a ventricle (S3), hypertension (S4), or the like.

Figure 2:
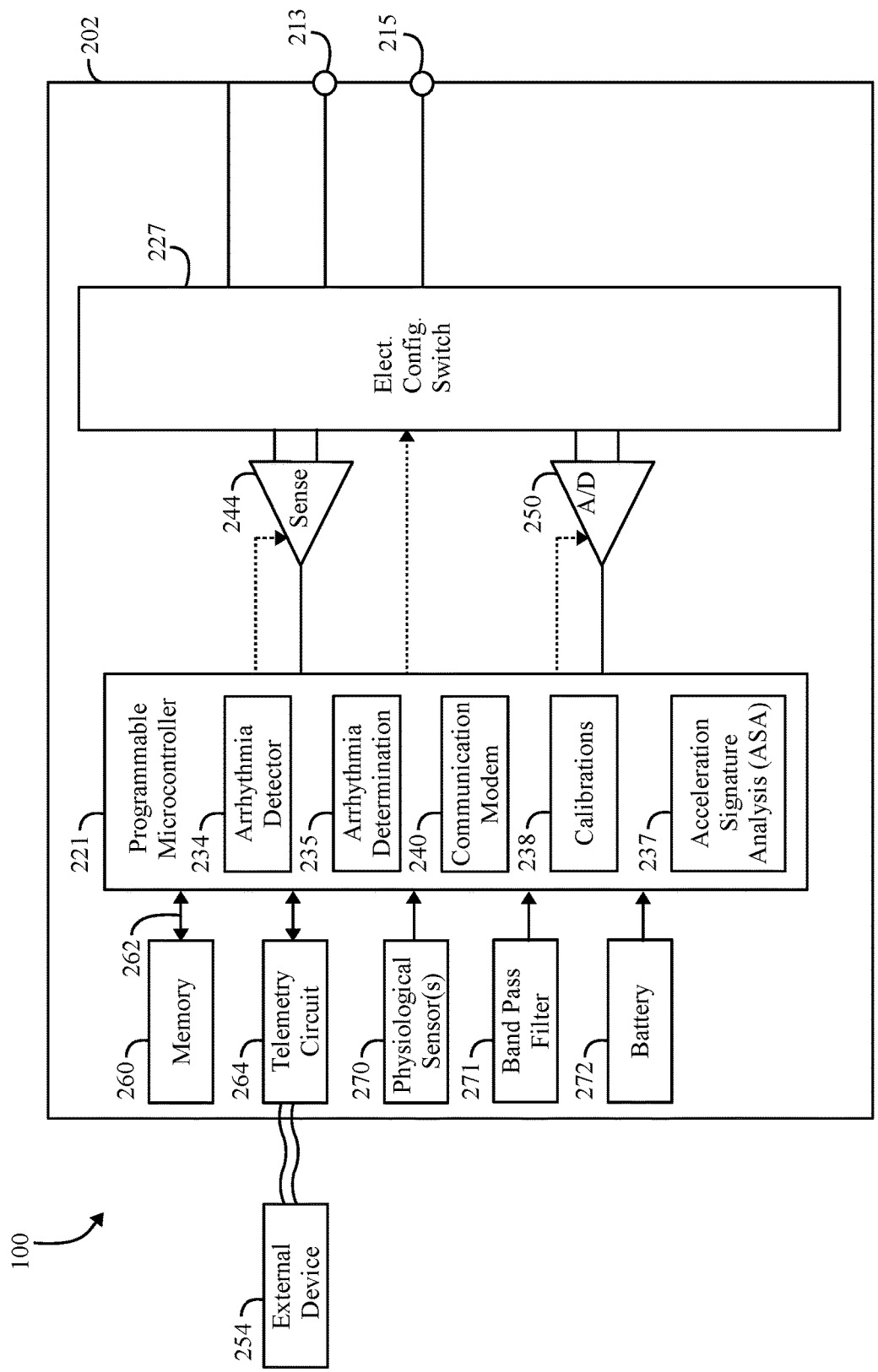
FIG. 2 illustrates a block diagram of the ICM formed in accordance with embodiments herein.

FIG. 2 shows an example block diagram of the IMD 100 formed in accordance with embodiments herein. The IMD 100 may be implemented to monitor ventricular activity alone, or both ventricular and atrial activity through sensing circuit. The IMD 100 has a housing 202 to hold the electronic/computing components. The housing 202 (which is often referred to as the "can," "case," "encasing," or "case electrode") may be programmably selected to act as an electrode for certain sensing modes. Housing 202 further includes a connector (not shown) with at least one terminal 213 and optionally additional terminals 215. The terminals 213, 215 may be coupled to sensing electrodes that are provided upon or immediately adjacent the housing 202. Optionally, more than two terminals 213, 215 may be provided in order to support more than two sensing electrodes, such as for a bipolar sensing scheme that uses the housing 202 as a reference electrode. Additionally or alternatively, the terminals 213, 215 may be connected to one or more leads having one or more electrodes provided thereon, where the electrodes are located in various locations about the heart. The type and location of each electrode may vary.

The IMD 100 includes a programmable microcontroller 221 that controls various operations of the IMD 100, including cardiac monitoring. Microcontroller 221 includes a microprocessor (or equivalent control circuitry), RAM and/or ROM memory, logic and timing circuitry, state machine circuitry, and I/O circuitry. Microcontroller 221 includes an arrhythmia detector 234 that is configured to analyze the far field cardiac activity signals to identify the existence of an arrhythmia. The microcontroller also includes arrhythmia determination circuitry 235 for analyzing the far field CA signals to assess a presence or absence of R-waves within the cardiac beats, declaring a candidate arrhythmia based on the absence of at least one R-wave from the cardiac beats, and evaluating the acceleration signatures for ventricular events (VEs) to re-access the absence of the at least one R-wave and based thereon confirming or denying the candidate arrhythmia. In particular, the arrhythmia determination circuitry 235 analyzes the far field CA signals to determine a candidate arrhythmia, and then utilizes the acceleration signatures of VEs to verify the determination. Consequently, arrythmia detection accuracy is increased.

The microcontroller 221 may also include an acceleration signature analysis (ASA) module 237 configured to implement one or more of the operations discussed herein. The ASA module is configured to be a computer implemented method for detecting arrhythmias in cardiac activity. The ASA module obtains far field cardiac activity (CA) signals, at electrodes of an IMD, in connection multiple cardiac beats and in connection with different IMD locations relative to gravitational force. The method obtains acceleration signatures, at a sensor of the IMD, indicative of heart sounds generated during the cardiac beats and obtains device location information, at the IMD, with respect to the gravitational force during the cardiac beats. The ASA processor 237 evaluates the acceleration signatures for ventricular events (VEs) to re-access the absence of the at least one R-wave so that a candidate arrhythmia determined by the arrythmia determination circuitry 235 may be confirmed or denied.

The microcontroller 221 may also include calibration circuitry 238 that obtains calibration acceleration signatures at an accelerometer, or physiological sensor 270 that is indicative of heart sounds generated in connection with postures of the patient. The postures may include supine, laying on a right side, laying on are left side, angled, or the like. In one example, the acceleration signatures are indicative of heart sounds generated in connection with first and second postures of a patient. After the calibration procedure, the calibration circuitry 238 utilizes the calibration acceleration signatures to determine an axis of the accelerometer associated with a current posture. Then confirmation acceleration signatures are obtained along the axis of the accelerometer 270 in connection with the analyzing the far field CA signals.

Although not shown, the microcontroller 221 may further include other dedicated circuitry and/or firmware/software components that assist in monitoring various conditions of the patient's heart and managing pacing therapies.

A switch 227 is optionally provided to allow selection of different electrode configurations under the control of the microcontroller 221. The electrode configuration switch 227 may include multiple switches for connecting the desired electrodes to the appropriate I/O circuits, thereby facilitating electrode programmability. The switch 227 is controlled by a control signal from the microcontroller 221. Optionally, the switch 227 may be omitted and the I/O circuits directly connected to the housing electrode and a second electrode.

The IMD 100 is further equipped with a communication modem (modulator/demodulator) 240 to enable wireless communication. In one implementation, the communication modem 240 uses high frequency modulation, for example using RF, Bluetooth or Bluetooth Low Energy telemetry protocols. The signals are transmitted in a high frequency range and will travel through the body tissue in fluids without stimulating the heart or being felt by the patient. The communication modem 240 may be implemented in hardware as part of the microcontroller 221, or as software/firmware instructions programmed into and executed by the microcontroller 221. Alternatively, the modem 240 may reside separately from the microcontroller as a standalone component. The modem 240 facilitates data retrieval from a remote monitoring network. The modem 240 enables timely and accurate data transfer directly from the patient to an electronic device utilized by a physician.

The IMD 100 includes sensing circuit 244 selectively coupled to one or more electrodes that perform sensing operations, through the switch 227 to detect cardiac activity data indicative of cardiac activity. The sensing circuit 244 may include dedicated sense amplifiers, multiplexed amplifiers, or shared amplifiers. It may further employ one or more low power, precision amplifiers with programmable gain and/or automatic gain control, bandpass filtering, and threshold detection circuit to selectively sense the features of interest. In one embodiment, switch 227 may be used to determine the sensing polarity of the cardiac signal by selectively closing the appropriate switches.

In the example of FIG. 2, a single sensing circuit 244 is illustrated. Optionally, the IMD 100 may include multiple sensing circuits, similar to sensing circuit 244, where each sensing circuit is coupled to two or more electrodes and controlled by the microcontroller 221 to sense electrical activity detected at the corresponding two or more electrodes. The sensing circuit 244 may operate in a unipolar sensing configuration or a bipolar sensing configuration. Optionally, the sensing circuit 244 may be removed entirely, and the microcontroller 221 perform the operations described herein based upon the CA signals from the ND data acquisition system 250 directly coupled to the electrodes. The output of the sensing circuit 244 is connected to the microcontroller 221 which, in turn, determines when to store the cardiac activity data of CA signals (digitized by the ND data acquisition system 250) in the memory 260. These CA signals are then analyzed to determine a candidate arrhythmia that may be verified by analysis of acceleration signatures as described herein.

The IMD 100 further includes an analog-to-digital ND data acquisition system (DAS) 250 coupled to one or more electrodes via the switch 227 to sample cardiac activity signals across any pair of desired electrodes. The ASA processer 237 may be applied to signals from the sensing circuit 244 and/or the DAS 250.

By way of example, the external device 254 may represent a bedside monitor installed in a patient's home and utilized to communicate with the IMD 100 while the patient is at home, in bed or asleep. The external device 254 may be a programmer used in the clinic to interrogate the IMD 100, retrieve data and program detection criteria and other features. The external device 254 may be a handheld device (e.g., smartphone, tablet device, laptop computer, smartwatch and the like) that can be coupled over a network (e.g., the Internet) to a remote monitoring service, medical network and the like. The external device 254 facilitates access by physicians to patient data as well as permitting the physician to review real-time CA signals while collected by the IMD 100.

The microcontroller 221 is coupled to a memory 260 by a suitable data/address bus 262. The memory 260 stores the acceleration signatures, reference posture data sets, cardiac activity signals, as well as the markers and other data content associated with detection and determination of the arrhythmia.

The IMD 100 can further include one or more physiologic sensors 270. For example, the physiologic sensor 270 may represent one or more accelerometers, such as a three-dimensional (3D) accelerometer. The sensor 270 may utilize a piezoelectric, a piezoresistive, and/or capacitive components are commonly used to convert the mechanical motion of the 3D accelerometer into an electrical signal received by the microcontroller 221. By way of example, the 3-D accelerometer may generate three electrical signals indicative of motion in three corresponding directions, namely X, Y and Z directions. The electrical signals associated with each of the three directional components may be divided into different frequency components to obtain different types of information therefrom.

The physiologic sensor 270 collects device location information with respect to gravitational force while the IMD collects cardiac activity signals in connection with multiple cardiac beats. The microcontroller 221 may utilize the signals from the physiologic sensor 270 in the manner described in U.S. Pat. No. 6,937,900, titled "AC/DC Multi-Axis Accelerometer For Determining A Patient Activity And Body Position," the complete subject matter which is expressly incorporated herein by reference. While shown as being included within the housing 202, the physiologic sensor(s) 270 may be external to the housing 202, yet still, be implanted within or carried by the patient.

The physiologic sensor 270 may be further configured to obtain acceleration signatures indicative of heart sounds generated during cardiac beats. The acceleration signatures from the sensor 270 are provided to the microcontroller 221 and are analyzed by the acceleration signature analysis process 237. In one example of the sensor 270 varies readings as a result of positioning of the patient. For instance, if the IMD is placed on a flat surface, the z-axis of the accelerometer indicates 1 g (gravity) while the x and y axis gravity data are zero because each axis is perpendicular to gravity. If the patient changes position, a new position is represented by a unique combination of x, y, z values with respect to gravity. As such, the position of IMD is indicative of gravity influencing 3-axis of the accelerometer that is unique to a particular position and is not the result of heart sound.

In one example, the accelerator signatures may be an AC-high frequency component from the 3-D accelerometer. The AC-high frequency component may represent a composite AC-high frequency component formed from a combination (e.g., a sum) of the AC-high frequency components from the three electrical signals. The composite AC-high frequency component generally represents the acceleration signature that is indicative of heart sounds produced during a corresponding cardiac cycle. The AC-high frequency component may include signals having a frequency of 10 KHz or more, and more preferably in the range of 10-100 kHz.

In yet another example, the three directional signals generated by the 3-D accelerometer may be passed through one or more bandpass filters 271 to separate the AC-high frequency component. The output of the bandpass filter 271, including primarily only AC-high frequency components, represents an acceleration signature indicative of heart sounds produced during a corresponding cardiac cycle. In one example, the sensor may couple to a bandpass filter 271 for each axis of the accelerometer. In one example, each bandpass filter 271 is the same for each axis, whereas in other examples, each bandpass filter 271 may be different for each axis of the accelerometer. In yet another example, the two bandpass filters may be identical for two axes, and third bandpass filter may be different for a third axis. In yet another example, each bandpass filter 271 may have two filter settings, with a first filter setting between 7.5-100 Hz and a second filter setting between 15-100 Hz. In such an example, the filter with the 7.5 Hz lower −3 dB is ideal for collecting higher frequency contents, such as provided by a first heart sound S3, whereas the filter with 15 Hz lower −3 dB is a better option in collecting higher frequency content such as a second heart sound S1 or S2 while minimizing low frequency drift, or noise. Therefore, depending on the desired content of the heart sound or frequency characteristics of heart sound data of interest, a different filter, or setting may be utilized. Specifically, the microcontroller 221 may command the bandpass setting based on operational and patient conditions.

Returning to FIG. 2, a battery 272 provides operating power to all of the components in the IMD 100. The battery 272 is capable of operating at low current drains for long periods of time. The battery 272 also desirably has a predictable discharge characteristic so that elective replacement time can be detected. As one example, the housing 202 employs lithium/silver vanadium oxide batteries. The battery 272 may afford various periods of longevity (e.g., three years or more of device monitoring). In alternate embodiments, the battery 272 could be rechargeable. See, for example, U.S. Pat. No. 7,294,108, titled "Cardiac event micro-recorder and method for implanting same", which is hereby incorporated by reference.

Figure 3:
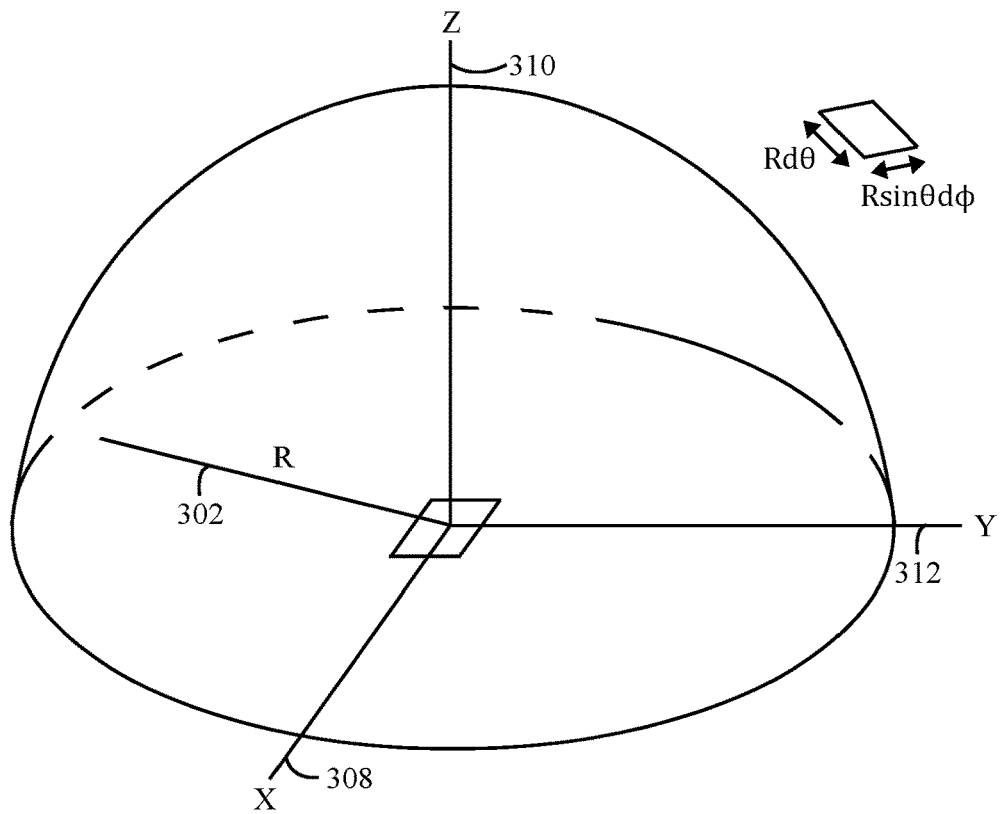
FIG. 3 illustrates force vectors experienced by the ICM in accordance with embodiments herein.

FIG. 3 illustrates force vectors experienced by the IMD 100 as determined by an accelerometer. The microcontroller 221 utilizes device location information, collected from the physiologic sensor 270, or accelerometer, to define a base local device coordinate system 300 for the IMD. The base local device coordinate system 300 may correspond to a global coordinate system and may be defined in terms of various types of coordinate systems, such as a Cartesian coordinate system, Polar coordinate system or otherwise. The microcontroller 221 defines the base local device coordinate system 300 relative to a reference vector 302 that corresponds to and is defined by, the gravitational force of earth. Regardless of the position and orientation of the IMD 100, the gravitational force of earth will remain constant and serve as a reference vector having a fixed magnitude and direction.

After implant, during a calibration procedure, a patient moves through a number of predefined postures that are configured to orient the IMD 100 in known positions and orientations with respect to the gravitational force. When the patient is at each of the predefined postures, the microcontroller 221 collects device location information from the physiologic sensor 270, providing location information in the X, Y and Z directions 308, 312, 310, relative to the Earth's gravitational force. The IMD 100 has an initial/reference position and orientation within the base local device coordinate system 300. For example, the initial/reference position and orientation may define an orientation of a longitudinal axis extending through a center of the IMD 100 and may define a position of a reference point on the IMD 100 (e.g., a distal or proximal tip, a center of mass, a center point on a select electrode and the like). After the calibration procedure, the calibration acceleration signatures are utilized to determine an axis of the accelerometer associated with a current posture. Then confirmation acceleration signatures are obtained along the axis of the accelerometer 270 in connection with the analyzing the far field CA signals.

Figure 4:
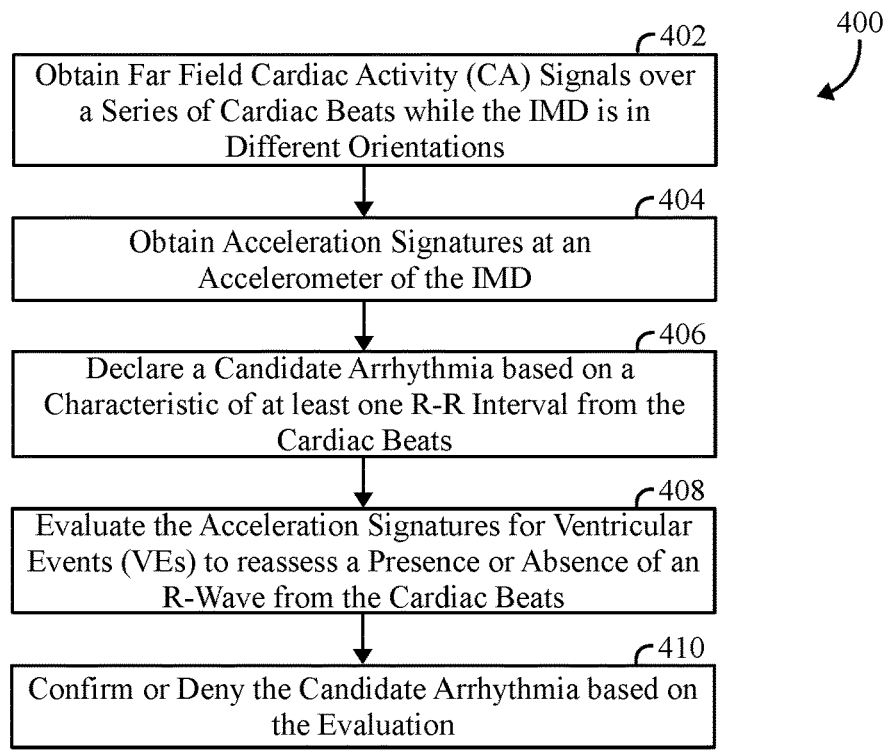
FIG. 4 illustrates a flow block diagram of a process of confirming or denying candidate arrhythmia based on an evaluation of acceleration signatures in accordance with embodiments herein.

FIG. 4 illustrates a flow block diagram of a method 400 of confirming or denying candidate arrhythmias based on an evaluation of acceleration signatures for ventricular events (VEs) to reassess a presence or absence of an R-wave from cardiac beats. In one example the method 400 is performed with heart sound data detected and retrieved utilizing the methods and systems described in detail in relation to FIGS. 1-3. All or a portion of the operations of FIG. 4 may be implemented by one or more processors in the IMD, one or more processors of the local external device and/or one or more processors of a remote server. Optionally, the operations of FIG. 4 may be divided between the IMD, local external device and remote server.

At 402, one or more processors of, or related to, an IMD obtain far field cardiac activity (CA) signals over a series of cardiac beats. Optionally, the far field CA signals may be received at the electrodes on an IMD and transmitted a local external device, a remote device, or the like. Based on the obtained far field CA signals features of interest of may be determined, including R-R interval, that may be utilized to declare an arrythmia.

At 404, the one or more processors obtain acceleration signatures at an accelerometer of the IMD. In an example, the one or more processors obtain the acceleration signatures from a predetermined axis, X, Y, or Z, of the accelerometer based on the posture of the patient. Specifically, this determination may be made utilizing methodologies described herein. The acceleration signatures may be used to determine 51 heart sound amplitudes, QRS to 51 heart sound intervals, or the like.

At 406, the one or more processors declare a candidate arrhythmia based on a characteristic of at least one R-R interval from the cardiac beats. In one example, the arrhythmia determination circuitry 235, upon determination of the at least one R-R interval characteristic transmits a signal to the one or more processors indicating the characteristic and that a candidate arrhythmia is declared. In one example, the at least one R-R interval characteristic is the length of time associated with each R-R interval. In one example, the candidate arrhythmia is an atrial fibrillation (AF). As an example, the candidate arrhythmia may be based on X out of Y CA signals determining the characteristic. In one example, four out of eight CA signals exceed a threshold length of time. Based on the at least one R-R interval characteristic from the cardiac beats the one or more processors declare the candidate arrythmia.

At 408, the one or more processors evaluate the acceleration signatures for VE events to reassess a presence or absence of an R-wave from the cardiac beats. In one example, evaluating the acceleration signatures includes determining at least one VE feature of interest based on the acceleration signatures and comparing the at least one VE feature of interest with predetermined VE confirmation criteria related to the at least one VE feature of interest. The VE features of interest may include amplitude variability of the S1 heart sound amplitude, variability of a QRS to S1 heart sound interval, a sensed R-wave, and/or the like.

At 410, the one or more processors confirm or deny the candidate arrhythmia based on the evaluation. When the evaluation of the acceleration signature identifies a heart sound indicating the presence of a corresponding VE during a beat segment that was not detected from the obtained far field CA signals, a previously declared candidate arrhythmia is denied. Alternatively, when the evaluation of the acceleration signatures identifies a heart sound indicating the absence of a corresponding VE during a beat segment as determined from the obtained far field CA signals, a previously declared candidate arrhythmia is confirmed.

Figure 5:
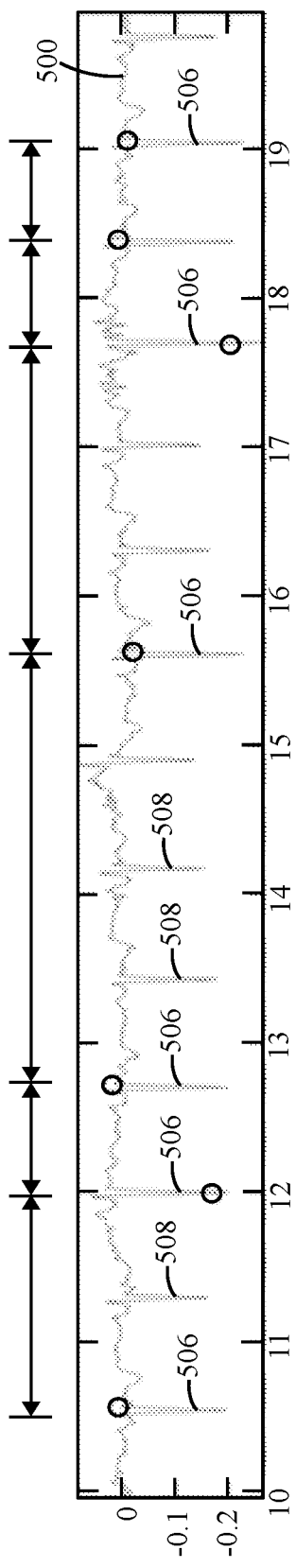
FIG. 5 illustrates a graph of R-Wave detection over time in accordance with embodiments herein.

FIG. 5 illustrates a graph of cardiac activity (CA) signals 500 that include R-waves over numerous heart beats wherein each circle indicates a detected R-wave 506, along with undetected R-waves 508. In the method 400, this graph illustrates the far field CA signals that are indicative of cardiac beats obtained at 402. In an example, the marking of the circle indicates a detected R-wave. Based on this obtained data, at 406, only five out of ten expected R-waves are detected, resulting in a candidate arrythmia to be declared.

Figure 6:
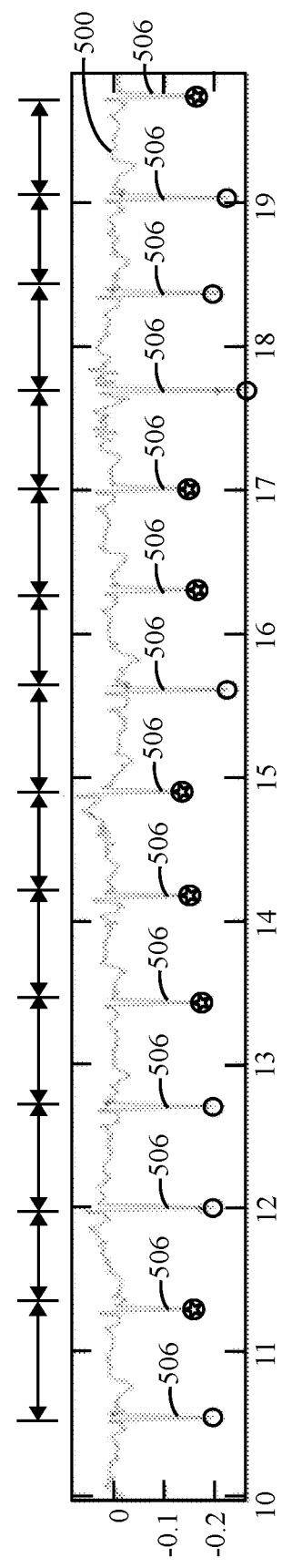
FIG. 6 illustrates a graph of R-Wave detection over time in accordance with embodiments herein.

FIG. 6 illustrates the graph of CA activity 500 when the one or more processors evaluate the acceleration signatures at 408 to confirm or deny the candidate arrhythmia. Specifically, as a result of using the acceleration signatures and the heart sound data, each R-wave is now detected. Therefore, by using the R-wave sensing provided within the heart sound data the presence of an under-sensing of the R-wave is provided. The graphs in FIGS. 5-6 illustrate how missed R-waves (graph of FIG. 5) can be identified (graph of FIG. 6) when monitoring associated heart sounds, including S1 heart sounds, QRS to S1 heart sound intervals, or the like that may be sensed by the accelerometer. Alternatively, over-sensing of the R-wave may similarly be determined. In an over-sensing of R-waves, noise, T-wave sensing, or the like cause additional interference that may be determined to be detected R-waves 506 by the one or more processors of an IMD when evaluating the far field CA signals. The S1 heart sound would be absent from the over-sensed R-waves. Consequently, by analyzing acceleration signatures and corresponding heart sound data, these additionally detected false R-waves 506 may be identified as noise, a T-wave, or the like by evaluating the acceleration signatures to ensure correct determinations. By using the acceleration signatures and heart sound data a declared candidate arrhythmia may be confirmed or denied. In one example, the heart sounds utilized includes at least one VE feature of interest that includes at least one of i) turbulence due to closure of a mitral valve and/or tricuspid value at a start of systole, ii) closure of aortic valve and/or pulmonic valve at an end of systole, iii) contraction (S1), iv) relaxation (S2), v) blood flowing into a ventricle (S3), or vi) hypertension (S4). In another example, the VE feature of interest of the heart sounds includes at least one of an S1 amplitude, an S1 frequency, a peak to peak timing between heart sounds in the acceleration signatures, or a ratio of heart sounds.

Figure 7:
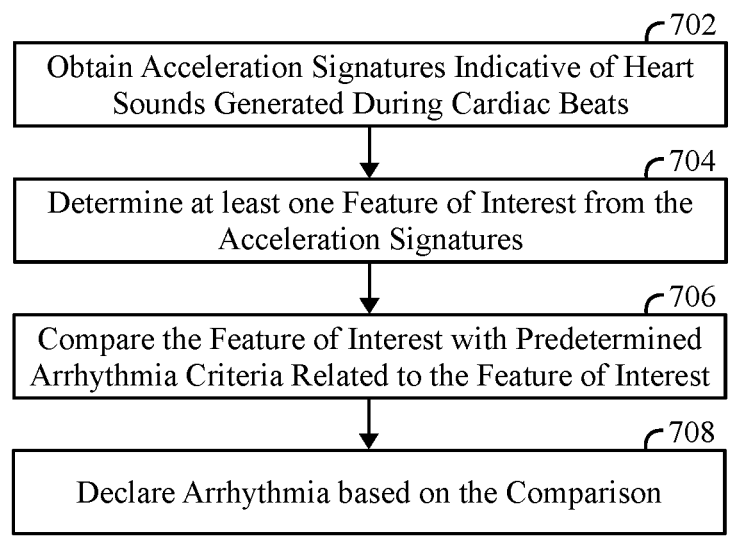
FIG. 7 illustrates a block diagram of a process of evaluating acceleration signatures to declare a candidate arrhythmia in accordance with embodiments herein.

FIG. 7 illustrates a process 700 of evaluating acceleration signatures to declare an arrhythmia. In an example, different heart sounds are utilized to determine VE features of interest, declare the arrhythmia. Specifically, the heart sound data may be evaluated to declare an arrhythmia without evaluation of the far field CA signals.

At 702, one or more processors obtain acceleration signals indicative of heart sounds generated during cardiac beats. In an example, the one or more processors obtain the acceleration signatures from a predetermined axis, X, Y, or Z, of an accelerometer based on the posture of the patient. Specifically, this determination may be made utilizing methodologies described herein. The acceleration signatures may be used to determine S1 heart sound amplitudes, QRS to S1 heart sound intervals, or the like.

At 704, one or more processors determine at least one feature of interest from the acceleration signals. In one example, the S1 amplitude variability is evaluated. Specifically, in normal sinus rhythms (NSR), beat to beat S1 heart sound amplitudes following R-waves are expected to be stable over time, whereas the amplitudes during an arrythmia such as AF, are expected to vary more. Therefore, in an example, the feature of interest is the amplitude of a S1 heart sound. In yet another example, the QRS to S1 interval variability is determined. Specifically, during an arrythmia such as AF, beat to beat QRS to S1 intervals are also expected to vary more than during NSRs similar to S1 heart sound amplitudes. In yet another example, both S1 heart sound amplitude variability and the QRS to S1 interval variability are determined.

At 706, one or more processors compare the feature of interest with predetermined arrhythmia criteria related to the feature of interest. In one example, S1 heart sound amplitudes over the heartbeats are obtained at 704, and compared to predetermined amplitudes for a healthy patient. Alternatively, the obtained S1 heart sound amplitudes are compared to S1 heart sound amplitudes of a patient experiencing an arrhythmia. In another example, the feature of interest is a QRS to S1 heart sound interval and the variability of QRS to S1 heart sound intervals are compared to the variability of the QRS to S1 heart sound intervals of a healthy patient, or of a patient experiencing an arrhythmia. In yet another example, both S1 heart sound amplitude variability and QRS to S1 heart sound interval variability are compared to S1 heart sound amplitude variability and QRS to S1 heart sound interval variability of a healthy patient and/or a patient experiencing an arrythmia.

At 708, one or more processors declare an arrythmia based on the comparison of the features of interest. In one example, when the S1 heart sound amplitudes of heartbeats over a predetermined interval vary above a predetermined threshold, the arrythmia is declared. In an example, a variance for each S1 heart sound amplitude from a mean heart sound amplitude over a minute interval is determined and averaged. That average variance in S1 heart sound amplitude is compared to an average variance in heart sound amplitudes of a healthy patient. If the average patient variance is greater than a threshold that in one example is 10% compared to the healthy patient, an arrythmia is declared. In another example, a QRS to S1 heart sound interval is obtained and variance of each QRS to S1 heart sound interval is compared to a mean QRS to S1 heart length to determine an average variance. The average variance is then compared to the average variance of a patient with an arrythmia, and if average variance is within a threshold, such as within a 5% threshold compared to the unhealthy patient, the arrythmia is declared.

Figure 8:
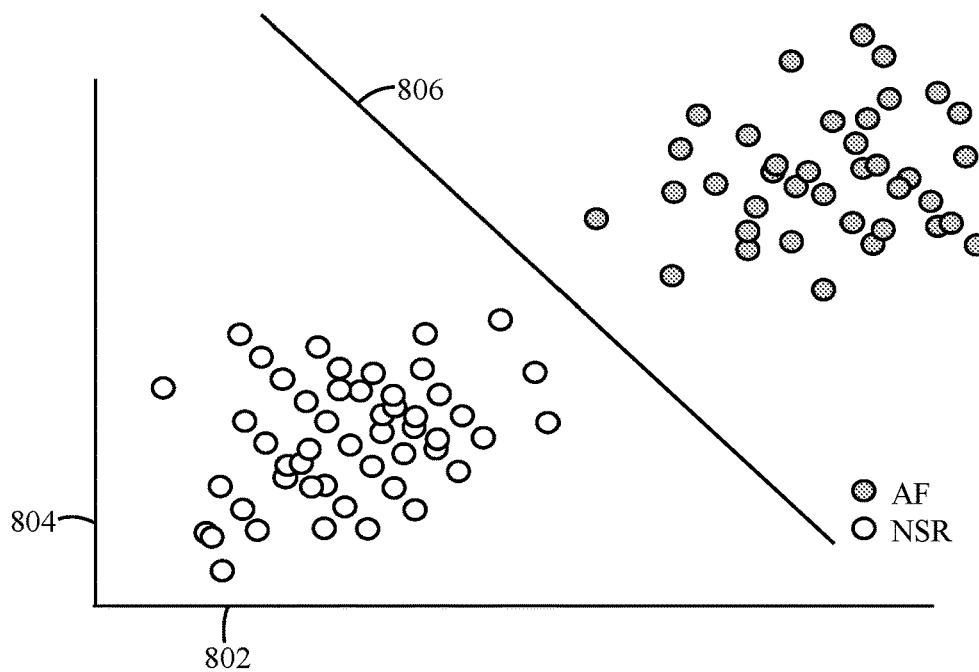
FIG. 8 illustrates a graph of interval variability vs. amplitude variability in accordance with embodiments herein.

FIG. 8 illustrates a graph of S1 heart sound amplitude variability 802 compared to QRS to S1 interval variability 804 that may result from the determination undertaken at 704. As illustrated, the black line represents the threshold line 806 that separates the arrythmia, or AF, and NSR. Therefore, in an example of 704, when both S1 heart sound amplitude variability 802 and QRS to S1 interval variability 804 are determined, at 708 a candidate arrythmia is declared when the combined S1 heart sound amplitude variability 802 and QRS to S1 interval variability 804 are to the right of the threshold line 806. Therefore, by utilizing heart sound data, an arrythmia may be declared.

Figure 9:
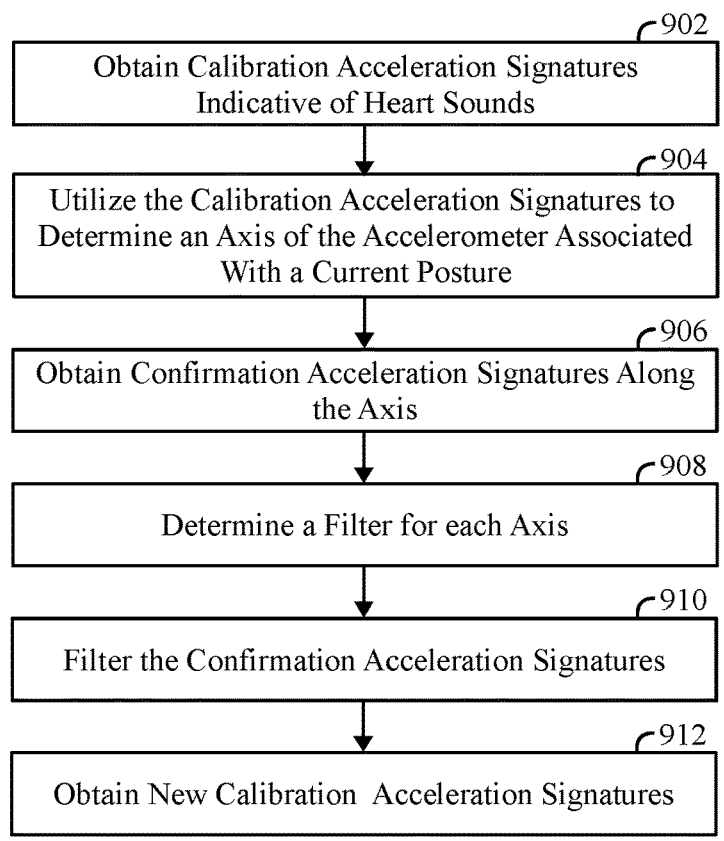
FIG. 9 illustrates a block flow diagram of a process for calibrating acceleration signatures in accordance with embodiments herein.

FIG. 9 illustrates a process for calibrating acceleration signatures in accordance with embodiments herein. All or a portion of the operations of FIG. 9 may be implemented by one or more processors in the IMD, one or more processors of the local external device and/or one or more processors of a remote server. Optionally, the operations of FIG. 9 may be divided between the IMD, local external device and remote server.

At 902, the one or more processors obtain calibration acceleration signatures, at an accelerometer of an IMD, indicative of heart sounds generated in connection with different postures of the patient. The calibration acceleration signatures are also obtained for plural postures, include supine, on a left side, on a right side, at an angle, including 45 degrees, or the like. For each posture, determinations are made related to each axis (X,Y,Z) of the accelerometer for each axis in order to determine the axis that provides the best acceleration signatures.

For example, the calibration acceleration signatures may be collected over a single cardiac beat such that the acceleration signature is indicative of the heart sounds (e.g., S1 Contraction, S2 Relaxation, S3 Blood flowing into the ventricle, S4 Hypertension), and ratios thereof, for one cardiac cycle. The processors are electrically coupled to a heart sound sensor, such as the physiologic sensor 270 (e.g., a 3D accelerometer). A heart sound of the subject can include an audible or mechanical noise or vibration indicative of blood flow through the heart or valve closures of the heart. As a result of obtaining the acceleration signatures for plural postures, an optimal axis or a combination of multiple axes for a given posture may be recorded and stored in one or more memories.

At 904, after the calibration procedure, the calibration acceleration signatures are used to determine an axis of the accelerometer associated with a current posture. In one example, the one or more processors determine the z-axis should be utilized to obtain heart sound data related to S1 and S2 heart sounds. In another example the one or more processors determine both the x-axis and y-axis should be utilized to obtain heart sound data related to S2 and S4 heart sounds. Additionally or alternatively, all three axes may be utilized. Similarly, the same axis may be utilized for each heart sound 51, S2, S3, and S4, or differing axes may be utilized for 51, S2, S3, and S4. Specifically, the z-axis may be utilized for sound 51 and S2 while the x-axis is used for sound S3 and the y-axis for sound S4. Consequently, the axis with the strongest signal is determined and selected, reducing false or incorrect readings from occurring by minimizing interference and lack of signal strength as a result of patient posture. To this end, optionally, the feedback filter associated with each axes may vary feedback setting based on the axis determined by the one or more processors.

At 906, confirmation acceleration signatures along the axis of the aceelerometer are obtained in connection with analyzing far field signals. The conformation acceleration signatures are presented to ensure that the IMD has not shifted in the subcutaneous pocket resulting in the need for recalibration.

At 908, a filter for each axis of the accelerometer is determined based on the calibration acceleration signatures. In one example, a signal to noise ratio for each axis is determined for a feature of interest of a heart sound. Then, based on the signal to noise ratio, the filter is determined. In one example, each axis of the accelerometer includes a bandpass filter with more than one setting. In yet another example, the two bandpass filters may have identical settings for two axes, and the third bandpass filter may have a different setting for a third axis. In yet another example, each bandpass filter may have two filter settings, with a first filter setting between 7.5-100 Hz and a second filter setting between 15-100 Hz. In such an example, the filter with the 7.5 Hz lower −3 dB is ideal for collecting lower frequency contents, such as provided by a first heart sound S3, whereas the filter with 15 Hz lower −3 dB is a better option in collecting higher frequency content such as a second heart sound S1 or S2 while minimizing low frequency drift, or noise. Therefore, depending on the desired content of the heart sound or frequency characteristics of heart sound data of interest, a different filter, or setting may be determined. In this manner, the one or more processors may determine the optimal setting for each bandpass filter in each position or posture immediately after implant. This information, or data may then be utilized during use of the IMD.

At 910, the confirmation acceleration signatures are filtered based on the determined filter. In one example, this includes switching the setting of a bandpass filter as determined. Therefore, enhanced detection of the acceleration signatures is achieved.

At 912, optionally, the over time, calibration acceleration signatures are obtained to account for shifts or movement of the IMD. As a result, axis determination is made periodically, or over predetermined intervals during use of the IMD. In particular, over time the position of the IMD, and consequently, the accelerometer, can change within a subcutaneous pocket. In one example, 904-910 are repeated after a predetermined interval, or intervals. Such determinations may be made at a clinician appointment or otherwise. In an example the interval is once every month. Alternatively, in another example, the position of the IMD within the subcutaneous pocket is monitored and upon detected movement of the IMD, 904-910 are repeated in response to such detected movement.

Figure 10:
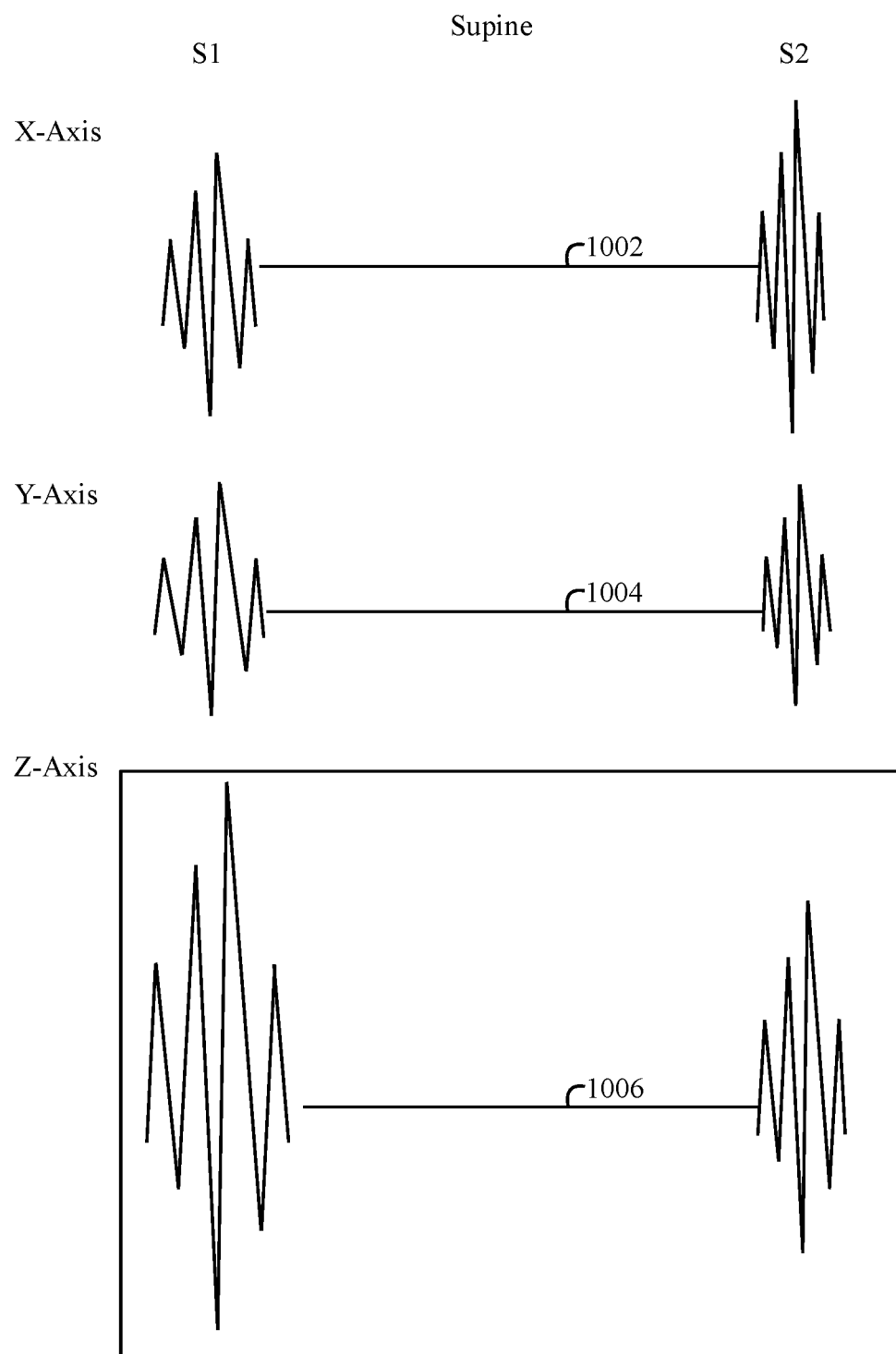
FIG. 10 illustrates a graph of heart sound over time taken along an axis of an accelerometer in accordance with embodiments herein.

FIG. 10 illustrates an example graph of acceleration signatures 1002, 1004, and 1006 detected on different axes of the accelerometer based on the posture of the patient. In FIG. 10, the patient is in a supine position and the acceleration signature 1006 on the Z-axis shows the strongest signal. When utilized in association with the process of FIG. 9, in one example, the one or more processors at 904 determine to use the Z-axis of the accelerometer when the patient is determined to have a supine posture.

Figure 11:
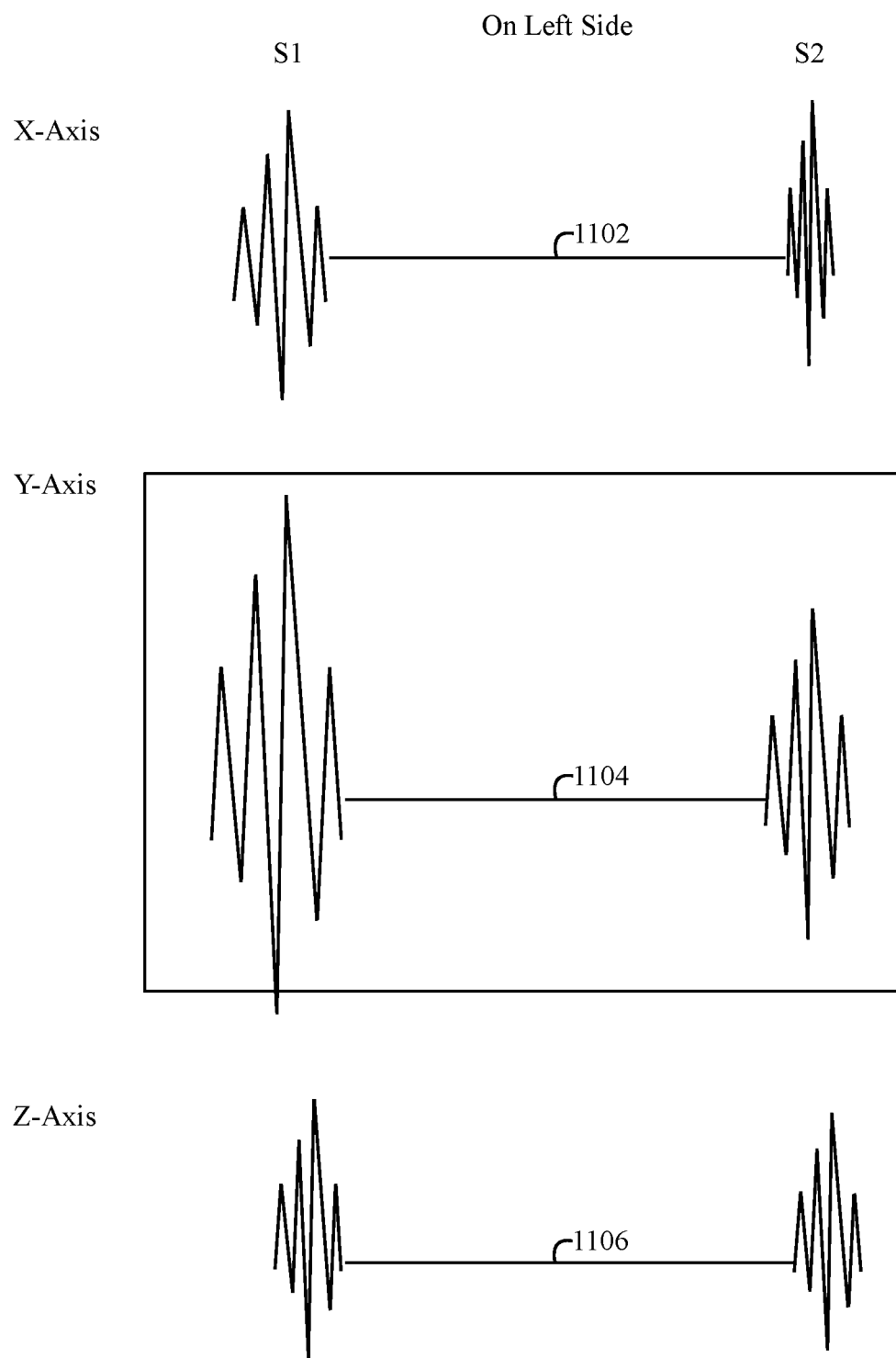
FIG. 11 illustrates a graph of heart sound over time taken along an axis of an accelerometer in accordance with embodiments herein.

FIG. 11 illustrates an example graph of acceleration signatures 1102, 1104, 1106 detected on different axes of the accelerometer based on the posture of the patient. In this example, the patient is on their left side and the Y-axis has the strongest acceleration signature. In an example when one or more processors determine that axis to use of accelerometer when the patient is on their left side, the one or more processors select the Y-axis.

Provided is an implantable medical device for arrythmia detection that utilizes heart sounds as detected by an accelerometer to verify the diagnosis of a potential arrythmia. At the time of implant the patient is monitored and posture data is taken in order to determine the best possible accelerometer axis or axes and bandpass filter setting for varying positions of the patient. Then during use of the IMD, one or more processors determine the position of the patient and utilizes the axis, axes, and/or bandpass filter setting to use to detect the heart sound data. Consequently, the quality of the heart sound data is increased, thereby reducing incorrect readings and verification of the arrythmia diagnosis. Additionally, throughout use, the position of the IMD is monitored for movement, and if movement is determined, the posture data is retaken in order to determine the best possible accelerometer axis or axes and bandpass filter setting for varying positions of the patient. As a result, improved quality of heart sound data is provided throughout the use of the IMD.

Such improved data procurement leads to increased uses of the heart sound data generated from the acceleration signatures, and specifically, features of interest of the heart sound data for diagnosing arrythmias. As an example, when QRS sensing by the IMD device is not accurate either over-sensing or under-sensing can occur, resulting in R-R variability. Such R-R variability sometimes increases to the point of diagnosing an arrythmia, such as atrial fibrillation (AF) inappropriately. Therefore, the heart sound data as described above, may be used to verify and prevent such misdiagnosis. In particular, S1 of heart sound represents atrioventricular valves closing during cardiac contraction, while true R-wave detections should be followed by subsequent ventricular contractions and associated S1 or S2 of heart sound. For example, as illustrated in the graph of FIG. 5, under-sensing of R-waves can occur in an IMD and lead to an inappropriate AF detection. Similarly, the missed R-waves in the graph of FIG. 6 are also associated with S1s which would be sensed by an accelerometer as illustrated in relation to the stars in the graph of FIG. 6. The resultant R-R wave variability with corrected R-wave sensing can be utilized to determine a candidate arrythmia is inaccurate because the variability is below the threshold for AF detection. Similarly, in an over-sensing of R-waves, such as due to the presence of noise or T wave sensing, S1 would be absent for over-sensed R-waves. Corrected R-wave sensing that removes over-sensed R-waves results in determining a candidate arrhythmia is incorrect.

In accordance with one more aspects herein, a system is provided for determining heart arrhythmias that includes one or more processors of an implantable medical device (IMD) configured with specific executable instructions to obtain acceleration signatures, at an accelerometer of the IMD, indicative of heart sounds generated during cardiac beats, evaluate the acceleration signatures by: determining at least one feature of interest of the acceleration signatures, wherein the at least one feature of interest includes amplitude variability of the acceleration signatures, or variability of a QRS to S1 heart sound interval. The one or more processors are also configured with specific executable instructions to compare the at least one feature of interest with predetermined arrythmia criteria, and declare an arrhythmia based on the at least one feature of interest.

Optionally, the one or more processors are configured with specific executable instructions to determine both the amplitude variability and the variability of the QRS to S1 heart sound interval. In another aspect, the one or more processors are configured with specific executable instructions to also identify a variability relation between the amplitude variability and the variability of the QRS to S1 heart sound interval, and compare the variability relation to a threshold line that separates atrial fibrillation (AF) arrhythmias and normal sinus rhythms.

Alternatively, the VE feature of interest includes at least one of an S1 amplitude, an S1 frequency, a peak to peak timing between heart sounds in the acceleration signatures, or a ratio of heart sounds. In another aspect the one or more processors are configured with specific executable instructions to obtain the acceleration signatures by, in connection with a calibration procedure, obtaining calibration acceleration signatures, at the accelerometer of the IMD, indicative of heart sounds generated in connection with first and second postures of a patient, and after the calibration procedure, utilizing the calibration acceleration signatures to determine an axis of the accelerometer associated with a current posture, and obtaining confirmation acceleration signatures along the axis of the accelerometer.

Optionally, the one or more processors are configured with specific executable instructions to also determine an axis of the accelerometer associated with a current IMD orientation, wherein to obtain the acceleration signatures includes obtaining the acceleration signatures along the axes determined.

CLOSING

It should be clearly understood that the various arrangements and processes broadly described and illustrated with respect to the Figures, and/or one or more individual components or elements of such arrangements and/or one or more process operations associated of such processes, can be employed independently from or together with one or more other components, elements and/or process operations described and illustrated herein. Accordingly, while various arrangements and processes are broadly contemplated, described and illustrated herein, it should be understood that they are provided merely in illustrative and non-restrictive fashion, and furthermore can be regarded as but mere examples of possible working environments in which one or more arrangements or processes may function or operate.

As will be appreciated by one skilled in the art, various aspects may be embodied as a system, method or computer (device) program product. Accordingly, aspects may take the form of an entirely hardware embodiment or an embodiment including hardware and software that may all generally be referred to herein as a "circuit," "module" or "system." Furthermore, aspects may take the form of a computer (device) program product embodied in one or more computer (device) readable storage medium(s) having computer (device) readable program code embodied thereon.

Any combination of one or more non-signal computer (device) readable medium(s) may be utilized. The non-signal medium may be a storage medium. A storage medium may be, for example, an electronic, magnetic, optical, electromagnetic, infrared, or semiconductor system, apparatus, or device, or any suitable combination of the foregoing. More specific examples of a storage medium would include the following: a portable computer diskette, a hard disk, a random access memory (RAM), a dynamic random access memory (DRAM), a read-only memory (ROM), an erasable programmable read-only memory (EPROM or Flash memory), a portable compact disc read-only memory (CD-ROM), an optical storage device, a magnetic storage device, or any suitable combination of the foregoing.

Program code for carrying out operations may be written in any combination of one or more programming languages. The program code may execute entirely on a single device, partly on a single device, as a stand-alone software package, partly on single device and partly on another device, or entirely on the other device. In some cases, the devices may be connected through any type of network, including a local area network (LAN) or a wide area network (WAN), or the connection may be made through other devices (for example, through the Internet using an Internet Service Provider) or through a hard wire connection, such as over a USB connection. For example, a server having a first processor, a network interface, and a storage device for storing code may store the program code for carrying out the operations and provide this code through its network interface via a network to a second device having a second processor for execution of the code on the second device.

Aspects are described herein with reference to the figures, which illustrate example methods, devices and program products according to various example embodiments. The program instructions may be provided to a processor of a general purpose computer, special purpose computer, or other programmable data processing device or information handling device to produce a machine, such that the instructions, which execute via a processor of the device implement the functions/acts specified. The program instructions may also be stored in a device readable medium that can direct a device to function in a particular manner, such that the instructions stored in the device readable medium produce an article of manufacture including instructions which implement the function/act specified. The program instructions may also be loaded onto a device to cause a series of operational steps to be performed on the device to produce a device implemented process such that the instructions which execute on the device provide processes for implementing the functions/acts specified.

The units/modules/applications herein may include any processor-based or microprocessor-based system including systems using microcontrollers, reduced instruction set computers (RISC), application specific integrated circuits (ASICs), field-programmable gate arrays (FPGAs), logic circuits, and any other circuit or processor capable of executing the functions described herein. Additionally, or alternatively, the modules/controllers herein may represent circuit modules that may be implemented as hardware with associated instructions (for example, software stored on a tangible and non-transitory computer readable storage medium, such as a computer hard drive, ROM, RAM, or the like) that perform the operations described herein. The above examples are exemplary only, and are thus not intended to limit in any way the definition and/or meaning of the term "controller." The units/modules/applications herein may execute a set of instructions that are stored in one or more storage elements, in order to process data. The storage elements may also store data or other information as desired or needed. The storage element may be in the form of an information source or a physical memory element within the modules/controllers herein. The set of instructions may include various commands that instruct the modules/applications herein to perform specific operations such as the methods and processes of the various embodiments of the subject matter described herein. The set of instructions may be in the form of a software program. The software may be in various forms such as system software or application software. Further, the software may be in the form of a collection of separate programs or modules, a program module within a larger program or a portion of a program module. The software also may include modular programming in the form of object-oriented programming. The processing of input data by the processing machine may be in response to user commands, or in response to results of previous processing, or in response to a request made by another processing machine.

It is to be understood that the subject matter described herein is not limited in its application to the details of construction and the arrangement of components set forth in the description herein or illustrated in the drawings hereof. The subject matter described herein is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

It is to be understood that the above description is intended to be illustrative, and not restrictive. For example, the above-described embodiments (and/or aspects thereof) may be used in combination with each other. In addition, many modifications may be made to adapt a particular situation or material to the teachings herein without departing from its scope. While the dimensions, types of materials and coatings described herein are intended to define various parameters, they are by no means limiting and are illustrative in nature. Many other embodiments will be apparent to those of skill in the art upon reviewing the above description. The scope of the embodiments should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects or order of execution on their acts.

What is claimed is:

1. A computer implemented method for determining heart arrhythmias based on cardiac activity, comprising:
    under control of one or more processors of an implantable medical device (IMD) configured with specific executable instructions,
    obtaining far field cardiac activity (CA) signals at electrodes located remote from the heart, the far field cardiac activity comprising, in part, normal sinus rhythms;
    obtaining acceleration signatures, at an accelerometer of the IMD, indicative of heart sounds generated during the cardiac activity;
    declaring a candidate arrhythmia based on a characteristic of at least one R-R interval from the normal sinus rhythms; and
    evaluating the acceleration signatures to identify heart sound (HS) indicated ventricular events to identify under-sensed or over-sensed ventricular events (VE) in the far field CA signals and to confirm or deny the declaring of the candidate arrhythmia.

2. The method of claim 1, wherein evaluating the acceleration signature includes determining at least one VE feature of interest of the acceleration signature and comparing the at least one VE feature of interest with predetermined VE confirmation criteria related to the at least one VE feature of interest to identify the under-sensed VE.

3. The method of claim 2, wherein the at least one VE feature of interest includes amplitude variability of the acceleration signatures, or variability of a QRS to heart sound interval.

4. The method of claim 1, further comprising at least one of i) denying the candidate arrhythmia when the evaluation of the acceleration signature identifies a first heart sound indicating a presence of a corresponding VE during an interval between successive first and second R waves in the at least one R-R interval, or ii) confirming the candidate arrhythmia when the evaluation of the acceleration signature does not identify a first heart sound indicating a presence of a corresponding VE during the interval between successive first and second R waves in the at least one R-R interval.

5. The method of claim 1, wherein the HS includes at least one VE feature of interest that includes at least one of i) turbulence due to closure of a mitral valve and/or tricuspid value at a start of systole, ii) closure of aortic valve and/or pulmonic valve at an end of systole, iii) contraction (S1), iv) relaxation (S2), v) blood flowing into a ventricle (S3), or vi) hypertension (S4).

6. The method of claim 5, wherein the HS includes a VE feature of interest corresponding to at least one of an S1 amplitude, an S1 frequency, a peak to peak timing between heart sounds in the acceleration signatures, or a ratio of heart sounds.

7. The method of claim 1, wherein the obtaining the acceleration signatures further comprises:
    in connection with a calibration procedure, obtaining calibration acceleration signatures, at the accelerometer of the IMD, indicative of heart sounds generated in connection with first and second postures of a patient; and
    after the calibration procedure:
        utilizing the calibration acceleration signatures to determine an axis of the accelerometer associated with a current posture; and
        obtaining confirmation acceleration signatures along the axis of the accelerometer in connection with the analyzing the far field CA signals.

8. The method of claim 1, further comprising:
    determining an axis of the accelerometer associated with a current posture; and
    determining a filter, for the axis of the accelerometer, based on the acceleration signatures; and filtering the acceleration signatures based on the filter.

9. The method of claim 8, wherein determining a filter for the axis of the accelerometer includes determining a signal to noise ratio for the axis of the accelerometer for a feature of interest of a heart sound.

10. The method of claim 1, wherein the declaring the candidate arrhythmia includes under-sensing the under-sensed R-wave in a beat segment and wherein the evaluating includes identifying a presence of the acceleration signature indicative of the corresponding heart sound that indicates a presence of the corresponding VE during the beat segment, for which the under-sensed VE, was not detected from the far field CA signals.

11. The method of claim 1, wherein the declaring the candidate arrhythmia includes over-sensing an over-sensed R-wave in a beat segment and wherein the evaluating includes identifying an absence of the acceleration signature and a corresponding absence of a corresponding VE during the beat segment, for which the over-sensed R-wave, was detected.

12. A system for determining heart arrhythmias based on cardiac activity, the system comprising:
    one or more processors; and
    a memory coupled to the one or more processors, wherein the memory stores program instructions, wherein the program instructions are executable by the one or more processors to:
    obtain far field cardiac activity (CA) signals at electrodes located remote from the heart, the far field cardiac activity comprising, in part, normal sinus rhythms;
    obtain acceleration signatures, at an accelerometer of the IMD, indicative of heart sounds generated during the cardiac activity;
    declare a candidate arrhythmia based on a characteristic of at least one R-R interval from the normal sinus rhythms; and
    evaluate the acceleration signatures to identify heart sound (HS) indicated ventricular events to identify under-sensed or over-sensed ventricular events (VE) in the far field CA signals and to confirm or deny the declaring of the candidate arrhythmia.

13. The system of claim 12, wherein, to evaluate the acceleration signatures, the program instructions are executable by the one or more processors to:

identify at least one an amplitude variability of the acceleration signatures, or a variability of a QRS to S1 heart sound interval.

14. The system of claim 13, wherein, to evaluate the acceleration signatures, the program instructions are further executable by the one or more processors to:

identify a variability relation between the amplitude variability and the variability of the QRS to S1 heart sound interval and comparing the variability relation to a threshold line that separates atrial fibrillation (AF) arrhythmias and normal sinus rhythms.

15. The system of claim 12, wherein, to obtain the acceleration signatures, the program instructions are executable by the one or more processors to:

in connection with a calibration procedure, obtain calibration acceleration signatures, at the accelerometer of the IMD, indicative of a heart sound generated in connection with first and second postures of a patient; and after the calibration procedure:
utilize the calibration acceleration signatures to determine an axis of the accelerometer associated with a current posture; and
obtain confirmation acceleration signatures along the axis of the accelerometer in connection with the analyzing the far field CA signals.

16. The system of claim 12, wherein the program instructions are executable by the one or more processors to evaluate the acceleration signature to:

determine an axis of the accelerometer associated with a current posture; and determine a filter for the axis of the accelerometer based on the calibration acceleration signatures; and filter the confirmation acceleration signatures based on the filter.

17. The system of claim 16, wherein, to determine a filter for the axis of the accelerometer, the program instructions are executable by the one or more processors to determine a signal to noise ratio for the axis of the accelerometer for a feature of interest of the heart sound.

18. The system of claim 17, wherein, to filter the confirmation acceleration signatures based on the filter, the program instructions are executable by the one or more processors to switch a setting of a bandpass filter.

19. The system of claim 17, wherein the feature of interest of the HS includes at least one VE feature of interest that includes at least one of i) turbulence due to closure of a mitral valve and/or tricuspid value at a start of systole, ii) closure of aortic valve and/or pulmonic valve at an end of systole, iii) contraction (S1), iv) relaxation (S2), v) blood flowing into a ventricle (S3), or vi) hypertension (S4).

20. The system of claim 12, wherein the program instructions are executable by the one or more processors to:

determine at least one feature of interest of the acceleration signatures, wherein the at least one feature of interest includes amplitude variability of the acceleration signatures, or variability of a QRS to S1 heart sound interval, wherein the determining comprises determining both the amplitude variability and the variability of the QRS to S1 heart sound interval;

compare the at least one feature of interest with predetermined arrhythmia criteria, wherein the comparing comprises identifying a variability relation between the amplitude variability and the variability of the QRS to S1 heart sound interval and comparing the variability relation to a threshold line that separates atrial fibrillation (AF) arrhythmias and normal sinus rhythms; and declare an arrhythmia based on the at least one feature of interest, wherein the feature of interest includes at least one of an S1 amplitude, an S1 frequency, a peak to peak timing between heart sounds in the acceleration signatures, or a ratio of heart sounds.

\* \* \* \* \*